United States Patent [19]
Mezrich et al.

[11] 3,969,578
[45] July 13, 1976

[54] VISUAL DISPLAY OF ULTRASONIC RADIATION PATTERN

[75] Inventors: Reuben Saul Mezrich, Rocky Hill, N.J.; Karl-Friedrich Etzold, New York, N.Y.; David Herman Raphael Vilkomerson, South Brunswick, N.J.

[73] Assignee: RCA Corporation, New York, N.Y.

[22] Filed: Mar. 14, 1975

[21] Appl. No.: 558,468

[30] Foreign Application Priority Data
Apr. 23, 1974 United Kingdom............... 17708/74

[52] U.S. Cl.............................. 178/6.8; 73/67.5 H; 178/DIG. 18
[51] Int. Cl.² ......................................... H04N 7/18
[58] Field of Search............... 178/6.8, DIG. 18, 7.1; 73/555, 556, 67.5 H, 67.8 S; 340/5 H, 5 MP

[56] References Cited
UNITED STATES PATENTS

| | | | |
|---|---|---|---|
| 3,571,493 | 3/1971 | Baker.................... | 178/7.1 |
| 3,716,826 | 2/1973 | Green................... | 73/67.5 H |
| 3,772,457 | 11/1973 | Macouski................. | 73/67.5 H |
| 3,831,135 | 8/1974 | Smith..................... | 178/DIG. 18 |

OTHER PUBLICATIONS
Fink, Donald G., Television Engineering Handbook, New York, McGraw–Hill 1957 pp. 3–35.

Primary Examiner—Howard W. Britton
Attorney, Agent, or Firm—Edward J. Norton; George J. Seligsohn

[57] ABSTRACT

Detection of peak phase change at ultrasonic frequency in two mutually coherent interfering light components, one of which is obtained by reflection from a rigid reference mirror and the other of which is obtained by reflection from a spot of a flexible pellicle mirror which is insonified by an ultrasonic radiation pattern, will provide an output proportional to the displacement amplitude of vibration of the spot of the pellicle, if, as is the case, the round trip optical path to the rigid reference mirror is wiggled through an excursion greater than one-half the wavelength of the coherent light at a frequency which is much lower than the frequency of the ultrasonic radiation insonifying the pellicle and the displacement amplitude is very many times smaller than the light wavelength. By raster scanning the spot over the area of the pellicle in synchronism with the raster scanning of the electron beam of a C.R.T., and at the same time intensity modulating the electron beam of the C.R.T. in accordance with the peak detected output, a two-dimensional visual display of the radiation pattern insonifying the pellicle is achieved.

15 Claims, 10 Drawing Figures

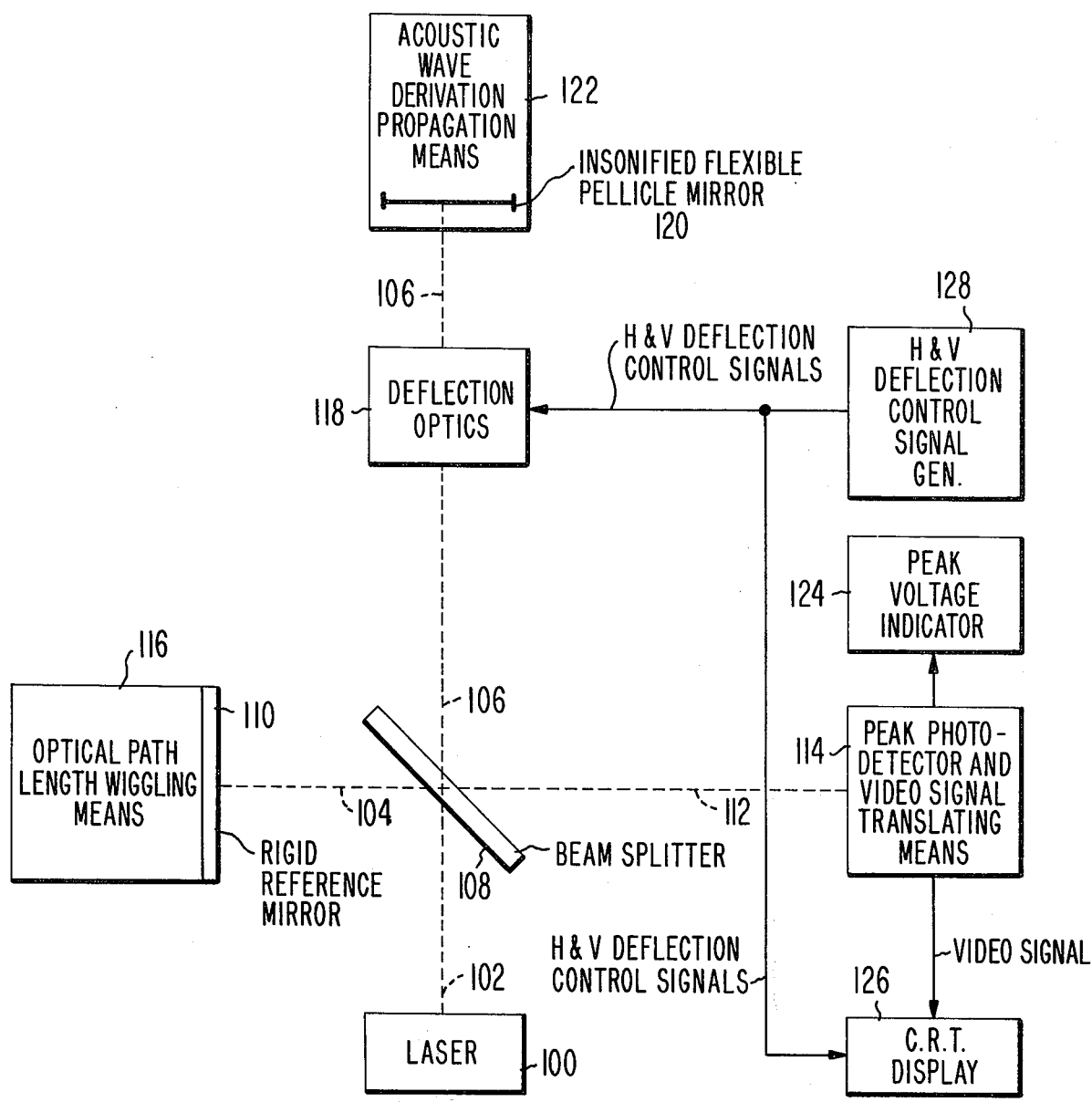
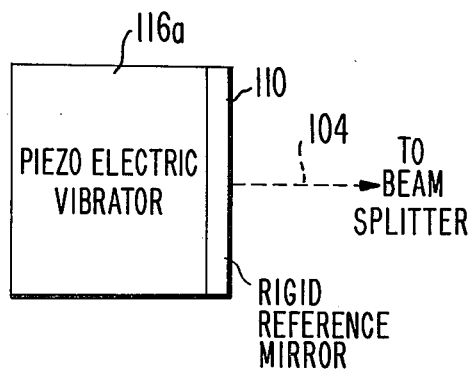
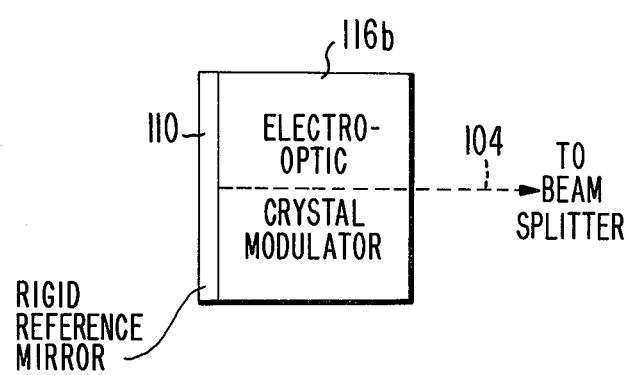
Fig. 1
Fig. 1a
Fig. 1b

VISUAL DISPLAY OF ULTRASONIC RADIATION PATTERN

This invention relates to the measurement of ultrasonic waves and, more particularly, to a technique capable of visually displaying the two-dimensional spatial distribution of the intensity of ultrasonic wave energy passing through a predetermined area.

The use of ultrasonics for the non-destructive testing of various types of three-dimensional objects, to discern the boundaries of regions therein having different propagation characteristics, is known in the art. Recently, such ultrasonic techniques have been employed in medical research for investigating pathological abnormalities, such as cancer, in tissue. In some cases, the tissue is a specimen obtained by a biopsy while in other cases the tissue is within the internal organs of a living person. (For an example of an ultrasonic wave-energy imaging technique that may be employed for imaging internal organs of a living person, see the copending U.S. patent application Ser. No. 406,218, entitled "Wave-Energy Imaging Technique", filed by Vilkomerson on Oct. 15, 1973 and assigned to the same assignee as the present invention.)

To properly design sophisticated instruments for the visualization of acoustic images there must first be the means to measure the characteristics of those elements that make up the instrument. The scattering characteristics of diffusers, the focussing properties of lenses, the angular spectrum of transducers are a few examples of the criteria that must be known in detail to properly design such a machine. The problems of measurement are compounded because the data must be collected over a two-dimensional aperture. The use of a single scanned transducer to make the measurements is laborious at best and ineffective in the main.

Ultrasonic cameras having the capability of two-dimensional imaging have been proposed. An example is the Sokolov tube, U.S. Pat. No. 2,164,125. Another is disclosed in the aforesaid Vilkomerson U.S. patent application Ser. No. 406,218. Although the two-dimensional ultrasonic imaging technique described in this patent application is particularly suitable for use as a diagnostic tool for imaging even the deeper internal organs of a human patient, due to its extremely high sensitivity, the technique disclosed therein is specialized and may not be practical in measuring the various characteristics of the elements making up an instrument for the visualization of the acoustic images. In general, all previous techniques having the capability of two dimensional ultrasonic imaging and visualization have failings in one or more areas. For example, some have narrow operating frequency ranges because they are based on resonance phenomenon, while others have limited angular response since they involve transmission of a wave through an interface.

The important parameters of an ultrasonic camera include: sensitivity, accuracy, angular response, resolution, dynamic range, and frequency range. The present invention relates to a device that allows the quantative and qualitative visualization of two-dimensional acoustic fields with the intensities as little as 5 nanowatts/cm$^2$. While this sensitivity is insufficient to permit imaging of the deep internal organs of a living human being, its sensitivity is still sufficiently high to permit the ultrasonic two-dimensional imaging of not-so-deep living tissue (hand, breast, etc.) and also biopsy tissue specimens, as well as being capable of measuring the aforesaid characteristics of elements that make up a sophisticated instrument for the visualization of acoustic images. In addition, the device of the present invention has the added advantage of being accurate to better than one db (as compared with the calibrated transducer) over an angular range of up to at least 50°. Further, it is linear over a range of intensities from as little as 5 nanowatts/cm$^2$ up to several watts/cm$^2$ and over a frequency range of at least 0.5 to 10 MHz (i.e. about 0.3–6 mm. acoustic wavelength in water).

Briefly, the present invention comprises an interferometer illuminated by a substantially coherent monochromatic light beam, preferably derived from a laser. The interferometer incorporates a beam splitter, a rigid mirror and a flexible mirror. The flexible mirror is illuminated with a light component from the beam splitter which is two-dimensionally deflected in accordance with applied deflection control signals. The flexible mirror may be a thin (6 micron) metalized plastic film or pellicle of relatively large area (e.g. 15 cm., i.e., several inches in diameter) which is located within a fluid medium through which the ultrasonic wave propagates. This flexible pellide mirror, which is located in the path of the ultrasonic wave, is so thin that it is essentially transparent to the ultrasonic wave, even for frequencies at least as high as 10 MHz, and for angles of incidence from 0° to beyond 50°. (Being transparent means that absorption or reflection of acoustic energy by the pellicle is negligible so that the pellicle motion, or displacment, is nearly equal to the displacement amplitude of the ultrasonic wave passing through it.) Thus, the spatial distribution of the displacement amplitude from point to point over the area of the surface of the flexible pellicle mirror is an analog of the spatial distribution of the ultrasonic wave energy itsself over the area covered by the pellicle.

The length of the optical path to the rigid mirror, which forms the reference mirror of the interferometer, is wiggled through a certain excursion at a predetermined frequency by such means as a vibrator or an electro-optic crystal. A peak photodetector detects the interference pattern produced by the light component reflected from the wiggling rigid reference mirror and the deflected light component reflected from the flexible pellicle mirror to derive a video signal. The video signal is used to intensity modulate the electron beam of a cathode-ray-tube (C.R.T.) display, which is two-dimensionally deflected in synchronism with the two-dimensional deflection of the light beam component illuminating the flexible pellicle mirror.

It has been found that an interferometer employing a wiggler provides a sensitive, stable and accurate means for displacement measurement. For instance, although the displacement amplitude of a 1.5 MHz acoustic wave of 5 nanowatts/cm$^2$ power density is less than 1 picometer (i.e. less than 1 percent of the nominal diameter, i.e. 1A, of a single atom), the system can still detect such a small displacement amplitude in a stable manner over an extended period of time. This is true despite the fact that random drift, due to such uncontrollable factors as air currents, thermal expansion and contraction of optical elements, etc., as well as variations from optical flatness in optical elements, introduce amplitude disturbances which may be many times larger than the displacement amplitudes to be measured.

These and other features and advantages of the present invention will become more apparent from the following detailed description taken together with the accompanying drawing, in which:

FIG. 1 is a block diagram of a system incorporating the principles of the present invention;

FIGS. 1a and 1b, respectively, illustrate first and second respective embodiments of the optical path length wiggling means of FIG. 1;

FIG. 2 schematically illustrates an embodiment of the focus and deflection optics of the system shown in FIG. 1;

Figure 2:
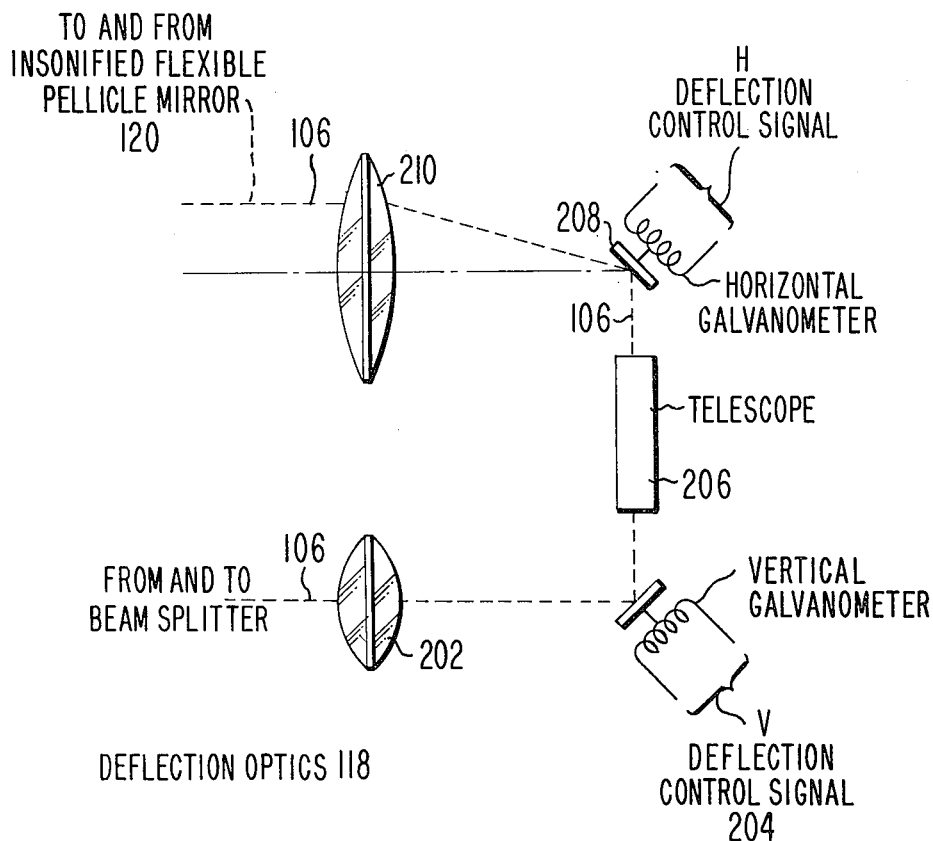

Referring now to the system shown in FIG. 1, there is shown laser 100, which may be a He-Ne gas laser, by way of example. Laser 100 emits coherent monochromatic light beam 102, at a predetermined wavelength, such as 6328A. Light beam 102 is split into mutually coherent first light component 104 and second light component 106 by beam splitter 108.

First light component 104 is reflected from rigid reference mirror 110, which is oriented normal to first light component 104, and returned to beam splitter 108. A portion of reflected first light component 104 passes through beam splitter 108 and travels over path 112 to the light sensing element of peak photodetector and video signal translating means 114. (This light sensing element may be a photodiode.)

The optical path length (the path length measured in wavelengths of the laser light) traveled by first light component 104 in making a round trip between beam splitter 108 and rigid reference mirror 110 does not remain constant, but is continuously varied at a predetermined frequency, which is much lower than the ultrasonic wave frequency, by an amount which, at the very least, is more than one-half the wavelength of the laser light being employed. (Thus, if the laser is a He-Ne laser operating at a wavelength of 6328A, the round trip change in optical path length should be about 3200A or more.) Optical path length wiggling means 116, shown associated with rigid reference mirror 110, provides the continuous variation in the optical path length between beam splitter 108 and rigid reference mirror 110. In practice, optical path length wiggling means 116 may take the form of a mechanical vibrator, such as piezoelectric vibrator 116a shown in FIG. 1a, or, alternatively, it may take the form of electro-optic crystal modulator 116b shown in FIG. 1b. Electro-optic crystal modulator 116b changes the optical path length by vibrating the index of refraction of the electro-optic crystal, such as KDP, incorporated therein. In any case, the peak-to-peak amplitude vibration of either rigid reference mirror 110 itself or the optical path length in wavelengths between beam splitter 108 and rigid reference mirror 110 need be only more than one-quarter of a wavelength of the laser light for the variation in the round trip optical path length between beam splitter 108 and rigid reference mirror 110 to exceed the required one-half wavelength of the laser light.

Second light component 106, after passing through deflection optics 118 (discussed below in connection with FIG. 2) is reflected from insonified flexible pellicle mirror 120 (incorporated in acoustic wave derivation and propagation means 122, discussed below in connection with FIGS. 3a, 3b and 3c) and returned through deflection optics 118 to beam splitter 108. Beam splitter 108 directs a portion of reflected second light component 106 incident thereon along path 112 to the light sensing element of peak photodetector and video signal translating means 114.

Thus, the total laser light directed along path 112 and incident on the light sensing element of peak photodetector and video signal translating means 114 is composed of a portion of first light component 104 reflected from wiggled rigid reference mirror 110 and a portion of second light component 106 reflected from insonified flexible pellicle mirror 120. These two light components, traveling together over path 112 and incident on the light sensing element of peak photodetector and video signal translating means 114, interfere with each other. Therefore, as is known in interferometry, the instantaneous amplitude of light sensed by the sensing element of peak photodetector and video translating means 114 at any instant of time depends on the phase difference (difference in optical path lengths) at that instant of time between the wave energy of the two incident light components. This phase difference varies in time as a function of both the wiggling displacement of rigid reference mirror 110 and the amount of acoustic vibration of the spot of insonified flexible pellicle mirror 120 then being illuminated by second light component 106. Further, this phase difference is subject to relatively slow random drift in the respective optical path lengths of the first and second light components, due to such uncontrollable factors as air currents, thermal expansion and contraction of optical elements, etc.

In any case, for reasons discussed in detail below, peak photodetector and video signal translating means 114 derives a voltage having a magnitude which is substantially proportional to the peak amplitude of the relatively high ultrasonic wave frequency modulation of the two interfering light components being sensed. (The d.c. component, as well as the relatively low random drift and wiggler frequency modulation of the two interfering light components are filtered out.) The magnitude of this peak amplitude voltage may be measured by peak voltage indicator 124, which may comprise an amplitude-calibrated oscilloscope, digital voltmeter, and/or other similar voltage measuring equipment. In addition, this detected peak voltage may be processed in a manner to be described below to provide a video signal which may be utilized to intensity modulate the electron beam of cathode ray tube display 126.

Cathode ray tube display 126 receives horizontal and vertical deflection control signals from horizontal and voltage deflection control signal generator 128. These horizontal and vertical deflection control signals are also applied to deflection optics 118 to control the position of the spot on insonified flexible pellicle mirror 120 at which second light component 106 is incident. Generator 128 may, alternatively, provide different types of horizontal and vertical control signals. By way of example, generator 128 may be operated to provide corresponding repetitive raster scans of both the entire surface of insonified flexible pellicle mirror 120 and the screen of cathode ray tube display 126. Typical raster scan frame rates, by way of example, would be from one fourth to 2 frames per second with each frame comprising 128 scan lines. Other alternative ways of operating generator 128 are (1) to provide a raster-scan of only a selected portion of the surface of insonified flexible pellicle mirror 128 or (2) to manually adjust the magnitudes of the horizontal and vertical control signals to continuously illuminate only a selected spot on the surface of insonified flexible pellicle mirror 120, while at the same time directing the video-signal intensity-modulated electron beam of cathode ray tube display 126 to a corresponding spot on the screen thereof.

Referring now to FIG. 2, there is shown an embodiment of deflection optics 118. Lens 202 is illuminated by second light component beam 106, which, as it arrives from beam splitter 108, normally has a substantially plane wavefront and a diameter of approximately one millimeter. Lens 202 focuses light component beam 106 at a point on the pivot axis of the mirror of vertical galvanometer 204 (which is angularly displaced in the vertical plane in accordance with the polarity and magnitude of the vertical deflection control signal applied to the coil thereof). The vertically deflected light reflected by the mirror of vertical galvanometer 204 is passed through telescope 206, which focuses this light at a point on the pivot axis of the mirror of horizontal galvanometer 208 (which is angularly displaced in the horizontal plane in accordance with the polarity and magnitude of the horizontal deflection control signal applied to the coil thereof). Therefore, the angular orientation of the deflected light reflected from the mirror of horizontal galvanometer 208 at any time is determined by the respective angular displacements of the mirrors of vertical galvanometer 204 and horizontal galvanometer 208 at that time. Collimating lens 210, which is illuminated by the deflected light beam from horizontal galvanometer 208, has its principal plane oriented substantially parallel to the plane of flexible pellicle mirror 120 and has an aperture which is normally at least as large as the surface area of flexible pellicle mirror 120. Therefore, collimated reflected second light beam component 106, emerging from collimating lens 210, illuminates any spot of flexible pellicle mirror 120 to which it is directed at normal incidence, regardless of the deflected position of the spot-illuminating light. This normal incidence ensures that the light reflected from flexible pellicle mirror 120 travels back to beam splitter 108 over the same path traveled by the spot-illuminating light beam (i.e., through lens 210, horizontal galvanometer 208, telescope 206, vertical galvanometer 204 and lens 202).

In practice, if the flexible pellicle mirror is perfectly smooth so that it specularly reflects, achieving the required parallel orientation between the principal plane of collimating lens 210 and the surface of flexible pellicle mirror 120 requires precise adjustment. The tolerance of this adjustment may be somewhat relaxed by making the surface of flexible pellicle mirror 120 slightly rough, so that it diffusely reflects to some extent. However, in this case, the light sensitivity of the system is somewhat reduced.

Usually, telescope 206 is composed of two lenses having substantially the same focal length. This results in the spot diameter of the light illuminating flexible pellicle mirror 120 being substantially the same as the diameter of second light beam component 106 arriving from beam splitter 108, (e.g. one millimeter). However, if desired, the relative focal length of the two lenses of telescope 206 may be varied to increase or decrease the diameter of the light spot on flexible pellicle mirror 120.

Figure 3A:
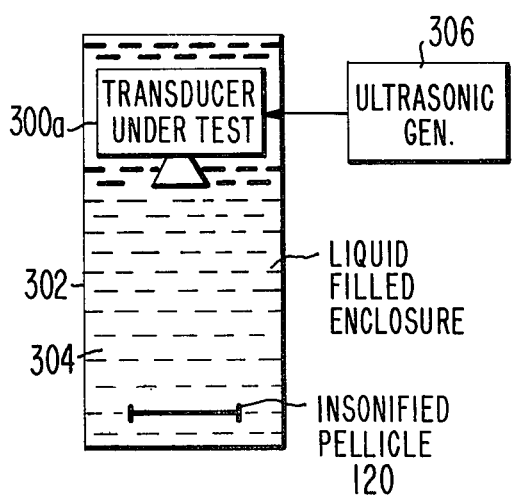
FIGS. 3a, 3b and 3c show respective examples of the acoustic wave derivation and propagation means shown in FIG. 1.
Figure 3B:
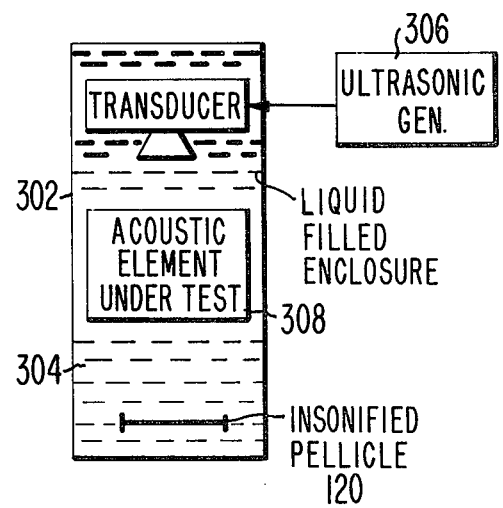
Figure 3C:
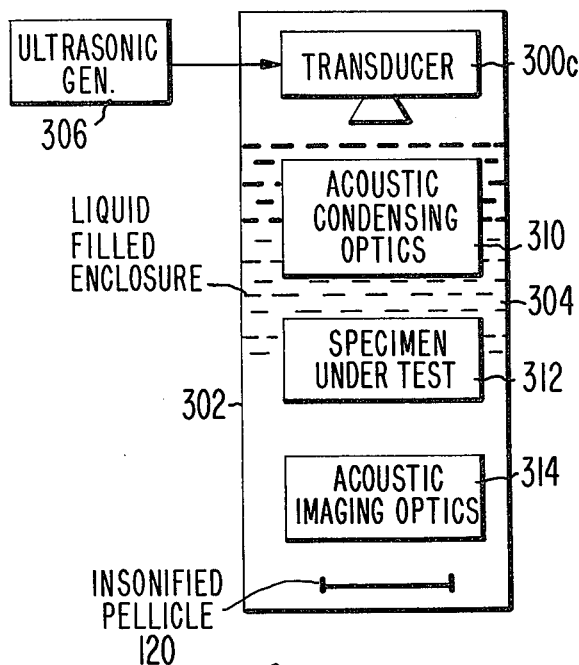

Illustrative examples of three different typical forms of acoustic wave derivation and propagation means 122 are shown in FIGS. 3a, 3b and 3c respectively. FIG. 3a shows the simplest case, where the radiation pattern of an ultrasonic transducer is to be ascertained. In this case, transducer under test 300a is placed in enclosure 302, which is filled with an ultrasonic wave propagating liquid 304, such as water. Transducer under test 300a is energized by wave energy at a suitable ultrasonic frequency between 0.5–10 MHz from ultrasonic generator 306. Also immersed in liquid 304 is insonified pellicle mirror 120, which forms the flexible mirror of the interferometer of FIG. 1.

As mentioned earlier, insonified pellicle mirror 120 may comprise a thin (6 micron) metalized plastic film of several inches in diameter. Besides being capable of reflecting the laser light incident thereon, each point of the pellicle vibrates at the frequency of the ultrasonic wave propagated in liquid 304 with a peak displacement amplitude which is determined by the intensity of the ultrasonic wave at that point. Therefore, the spatial distribution pattern of the peak amplitudes of vibration of insonified pellicle mirror 120 over its entire surface area is a measure of the ultrasonic radiation pattern of transducer under test 300a over this area.

FIG. 3b is directed to a somewhat more complex arrangement, where transducer 300b is a calibrated transducer, whose radiation characteristics are already known, and an acoustic element under test 308, such as a diffuser, acoustic lens arrangement, or any other acoustic element or elements which modify the radiation pattern of transducer 300b are immersed in liquid 304 between transducer 300b and insonified pellicle 120. In this case, the spatial distribution of the ultrasonic field over the area of insonified pellicle 120 is a measure of the modifying effect of the acoustic element under test 308.

An even more complex arrangement is shown in FIG. 3c. In this case, the ultrasonic wave energy emitted by transducer 300c, after being condensed by acoustic condensing optics 310, is used to insonify a specimen under test 312, which may be a tissue sample obtained by biopsy. In general, specimen under test 312 will have different ultrasonic wave energy attenuating characteristics at different points over its cross section. Therefore, the spatial distribution of the ultrasonic wave energy transmitted through specimen under test 312 constitutes an ultrasonic wave pattern which defines the ultrasonic characteristics of the insonified specimen under test 312. Acoustic imaging optics 314 projects a real image of this pattern on insonified pellicle 120 as a spatial distribution of peak amplitudes of ultrasonic vibration over the surface area of insonified pellicle 120.

Figure 4:
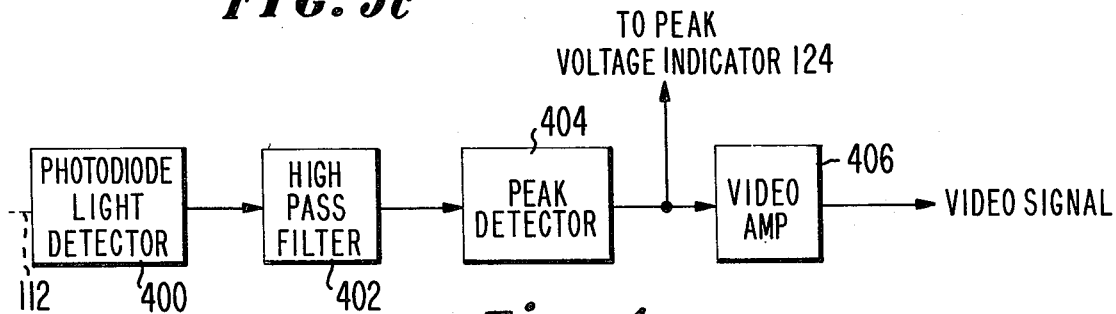
FIG. 4 shows an embodiment of the peak photodetector in video signal translating means of the system shown in FIG. 1.

Depending upon the mode of operation of the system shown in FIG. 1, the specific structure of peak photodetector and video signal translating means 114 may vary in certain respects. However, as shown in FIG. 4, peak photodetector and video signal translating means 114 normally includes photodiode light detector 400, high pass filter 402, peak detector 404 and video amplifier 406. The photodiode of light detector 400 senses the interfering light components directed thereto over path 112 and incident thereon.

The output from photodiode light detector 400 comprises a d.c. component, a relatively low frequency component and a relatively high frequency component. The relatively low frequency component includes the wiggler frequency itself, which varies in phase in accordance with random drift (i.e., the light-detected wiggler frequency is frequency modulated by the random drift). The low frequency component also includes raster scan frequencies, which are appreciably lower than the wiggler frequency. The high frequency component includes the ultrasonic wave frequency, which is amplitude modulated at the wiggler frequency and at the raster scan frequencies.

The output from photodiode light detector 400 is applied to high pass filter 402, which filters out the d.c. component and the low frequency component, but passes the high frequency component. The high frequency component from high pass filter 402 is then applied as an input to peak detector 404. Peak detector 404 includes an integrating circuit responsive to the detected peak amplitude of the applied ultrasonic wave, as is conventional. This integrating circuit may comprise a sample and hold circuit which is operated at a periodic rate sufficient to permit the detected peak voltage to follow the relatively slow changes in the peak amplitude envelope due to the scanning of the spot of light over the surface of insonified pellicle mirror 120.

As further shown in FIG. 4, the output from peak detector 404, which is proportional to the peak displacement amplitude of the insonified pellicle at the spot then being illuminated, is applied both as an input to peak voltage indicator 124 and as an input to video amplifier 406. The output from video amplifier 406 comprises the video signal which is applied as the electron-beam intensity modulating signal to cathode ray tube display 126, as shown in FIG. 1.

The operation of the system of the present invention, as so far described, will now be discussed. Although the system is capable of operating over at least a range of ultrasonic frequencies from 0.5–10 MHz, for illustrative purposes in describing the operations of the system, it will be assumed that the ultrasonic wave energy has a typical frequency of about 1.5 MHz.

As is known in the art of interferometry, a phase displacement of one interfering wave with respect to the other interfering wave produces a change in resultant amplitude and intensity which is a function of both the amount of such phase displacement and the initial phase relationship between the two interfering waves. More specifically, since light waves have a sinusoidal waveform, a given incremental phase displacement of one interfering wave with respect to the other produces a maximum change in the resultant amplitude and intensity when the two interfering waves are initially 90° out of phase with each other and produces a minimum change in amplitude and intensity when the two interfering waves are initially either in phase with each other or 180° out of phase with each other, because a sinusoidal wave has its maximum slope when it crosses the zero axis and a zero slope at its positive and negative peaks. Furthermore, because of the shape of a sinusoidal waveform, the linearity of this change in resultant amplitude with respect to phase displacement of the two interfering waves is highest when the two interfering waves are initially 90° out of phase with each other and is lowest when the two interfering waves are initially in phase with each other or 180° out of phase with each other.

A single wavelength of light (400–700 nanometers) is ordinarily considered an extremely short distance. However, the present invention is concerned with accurately measuring a minimum displacement smaller than 1 picometer, (less than $10^{-5}$ times as small as a wavelength of light) up to a maximum displacement of only about 12,500 picometers (about 1/40 of a wavelength of light). In order to accurately measure such a small quantity, it is essential that the measurement be made under stable interferometric conditions at which both the sensitivity and linearity of the measurements is high, i.e. where the two interfering waves are initially at least nearly 90° out of phase relative to each other. However, various types of uncontrollable factors, such as air current, thermal expansion and contraction of optic elements, etc., which create random drift in the respective lengths of the optical paths traveled by the two interfering waves, make it impossible to stably maintain the initial phase of the two interfering signals at near the desired 90° out-of-phase relationship. It is the optical path length wiggling of rigid reference mirror 110 over greater than one-half light wavelength, together with peak detection of the resultant amplitude of the high frequency component of the interfering waves which, in accordance with the principles of the present invention, makes it possible to solve this problem and actually achieve stable accurate measurements of the very small distance displacements of the insonified pellicle.

As mentioned earlier, the round trip optical pathlength to rigid reference mirror 110 is wiggled by an amount which, at the least, is more than one-half wavelength of the laser light. This wiggling ensures that at least once during each wiggling half-cycle the phase of one interfering wave will be exactly 90° out of phase with respect to the other interfering wave. The predetermined frequency of optical path length wiggling should be much smaller than the frequency of the ultrasonic wave being measured, but still be sufficiently high with respect to any scanning frequency of insonified flexible pellicle mirror 120 so that at least one-half cycle of optical path wiggling occurs in the scanning through a distance equal to the spot diameter of second light component 106 over insonified flexible pellicle mirror 120.

In the assumed case, the ultrasonic wave frequency is 1.5 MHz. A typical light spot diameter is about one millimeter the length of a scan line on insonified flexible pellicle mirror 120 is normally several inches, the maximum scanning rate is normally 128 lines per frame and 2 frames per second. With these values, an optical path length wiggling frequency of about 25 kHz operates satisfactorily. It is to be noted that this 25 kHz optical path length wiggling frequency is very much smaller than the 1.5 MHz ultrasonic wave frequency, but is still sufficient to permit each successive spot in a scan to be sampled at least once during each wiggling half-cycle (with the sampling taking place when one interfering wave is 90° out of phase with the other interfering wave).

Due to the much higher frequency of the ultrasonic wave energy with respect to the wiggler frequency, a multitude of ultrasonic cycles taking place during each wiggle cycle. Although the peak detector of means 114 is operative throughout each wiggle cycle, it is plain that the highest detected peak amplitude occurs at that point (or points), where one interfering wave is exactly 90° out of phase with the other inferfering wave. The linearity is also greatest at this point. Therefore, the output of the peak detector, which manifests only the highest peak, is proportional to the displacement amplitude of the spot on insonified flexible pellicle mirror 120 which is then being illuminated by focused second light component 106.

As discussed above, in connection with FIG. 4, the peak amplitude output of the peak detector responds to the scanning of insonified flexible pellicle mirror 120 by the deflected second light component 106 to provide at least one sample during the time (e.g. 50 microseconds) it takes to scan through each successive light spot area diameter. In this manner, the output of the peak detector constitutes a video signal which continuously manifests the displacement amplitude of the ultrasonic wave at each successively scanned spot of insonified flexible pellicle mirror 120.

This video signal after passing through video signal translating means, such as a video amplifier, is employed to intensity modulate electron beam of cathode ray tube display 126. At the same time, the electron beam is deflected in correspondence with the deflection of focused light component 106 incident on insonified flexible pellicle mirror 120. This results in CRT display 126 displaying a visual image pattern which corresponds to the ultrasonic wave pattern insonifying flexible pellicle mirror 120.

In addition, the output from peak photodetector of means 114 may be applied directly to peak voltage indicator 124 to obtain a measure which corresponds to the absolute peak amplitude of vibration of any spot on insonified flexible pellicle mirror 120.

It is important that the operation of optical path length wiggling means 116 not introduce any significant power at higher harmonics of the fundamental wiggling frequency in the vicinity of the ultrasonic wave frequency, since the presence of these higher harmonics would distort the high frequency component of the interference pattern measured by the peak photodetector of means 114.

Figure 5:
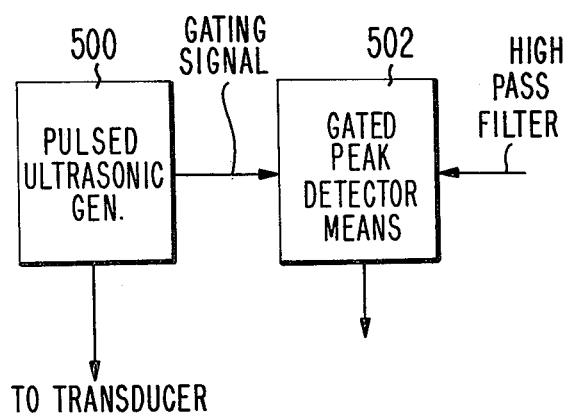
FIG. 5 shows a modification of the arrangement shown in FIG. 4 for use with pulsed ultrasonic wave energy.

One mode of actual operation of the system shown in FIG. 1 makes use of a pulsed ultrasonic wave source. The reason for this is that there is a tendency for insonified flexible pellicle mirror 120 to pick up unwanted reverberations, (i.e., echo patterns), due to reflection off the walls of the liquid filled enclosure. This problem may be obviated, in a manner similar to that employed in "range-gated" radar, by employing a relatively short duty cycle pulsed ultrasonic generator 500, shown in FIG. 5, to provide ultrasonic wave energy to the ultrasonic transducer in the liquid filled enclosure. At the same time, a gated peak detector means 502 is employed in peak photodetector and video signal translating means 114, to render gated peak detector means 502 enabled only in the presence of a gating signal applied as an input thereto from pulsed ultrasonic generator 500. Pulsed ultrasonic generator 500 applies an enabling gating pulse to gated peak detector means 502 at a predetermined time delay after the occurrence of each pulse of ultrasonic generator 500 which is just sufficient for the ultrasonic wave energy to travel from the transducer through the liquid of the liquid filled enclosure to the insonified pellicle shown in FIGS. 3a, 3b and 3c. The width of this gating pulse is at the most only slightly greater than the width of the pulse of ultrasonic wave energy, so that gated peak detector means 502 will be operative during the entire time that pellicle 120 is being insonified by the primary radiation pattern but not at other times. Therefore gated peak detector means 502 is disabled by the time that pellicle 120 is insonified by any reverberation patterns of ultrasonic wave energy.

Figure 6:
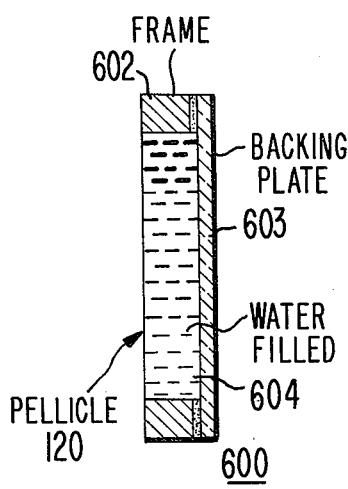
FIG. 6 shows a modified structural arrangement of the pellicle.

It may be desirable to make the pellicle insensitive to low frequency acoustic noise waves, which have a tendency to build up in liquid 304. There is shown in FIG. 6 a pellicle assembly 600, which may be employed in the arrangements of FIGS. 3a, 3b, and 3c. Pellicle assembly 600 does not respond to low-frequency acoustic noise waves. In particular, pellicle assembly 600 consists, for example, of an annular frame 602, covered in front by pellicle 120 itself, and covered in back by backing plate 603. This defines an interior central volume 604 in pellicle assembly 600 which is filled with water. Pellicle assembly 600 increases the effective stiffness of pellicle 120, so that it is insensitive to the low frequency vibrations of acoustic noise waves which build up due to "slop" of liquid 304 in enclosure 302.

Reference is made to the following appendix which sets forth mathematical formula supporting the principles of the present invention described herein. This appendix is incorporated as part of the complete specification.

APPENDIX

1. Formula for intensity of acoustic wave $$I_s = \tfrac{1}{2} Z\omega_s^2 \Delta^2 \tag{1}$$

where $I_s$ is intensity of acoustic wave, $Z$ is the acoustic impedance of the propagating medium $\omega_s = 2\pi f_s$, $f_s$ is the acoustic frequency, and $\Delta$ is the peak displacement amplitude.

2. Formula for instantaneous displacement of vibrating spot on pellicle, assuming no reflection and full transmission $$d = \Delta \cos \omega_s t \tag{2}$$

where $d$ is the instantaneous displacement, and $t$ is time.

3. Formula for interfering pellicle wave component $$a_p = A_p e^{j(\phi_p + 2\Delta \cdot \tfrac{2\pi}{\lambda} \cos(\omega_s t))} \tag{3}$$

where $a_p$ is the complex amplitude of the interfering light wave component reflected from pellicle, $A_p$ is the absolute amplitude thereof, $\phi_p$ is an arbitrary constant phase related to optical path length between pellicle and beam splitter, $\lambda$ is the wavelength of the light, and the first "2" factor arises from the fact that the relative phase shift due to acoustic vibration of pellicle is doubled on reflection.

4. Formula for interfering reference wave component $$a_r = A_r e^{j\phi_r} \tag{4}$$

where $a_r$ is the complex amplitude of the interfering light wave component reflected from reference mirror, $A_r$ is the absolute amplitude thereof; $\phi_r$ is an arbitrary constant phase related to optical path length between reference mirror and beam splitter.

5. Total light intensity measured by photodiode $$I_L = (a_2 + a_p)^2 \tag{5a}$$

$$2A_rA_p\sin(\phi_0+\phi_\omega\cos(W_\omega t))\sin(2\Delta \cdot \frac{2\pi}{\lambda}\cos(\omega_s t))$$

$$= |A_r|^2 + |A_p|^2 + 2A_rA_p\cos(\phi_p - \phi_r + 2\Delta \cdot \frac{2\pi}{\lambda}\cos(\omega_s t)) \tag{5b}$$

where $I_L$ is the total light intensity, $|A_r|^2 = I_{Lr}$, $I_{Lr}$ is the intensity of the reference mirror interfering light component, $|A_p|^2 = I_{Lp}$, $I_{Lp}$ is the intensity of the pellicle interfering light component.

6. In the case where $(\phi_p - \phi_r) = \pm 90°$, formula 5(b) becomes $$I_L = I_{Lr}+I_{Lp}+2\sqrt{I_{Lr}I_{Lp}}\cos\left(90° + 2\Delta \cdot \frac{2\pi}{\lambda}\cos(\omega_s t)\right) \tag{6a}$$

$$= I_{Lr} + I_{Lp} + 2\sqrt{I_{Lr}I_{Lp}}\sin\left(2\Delta \cdot \frac{2\pi}{\lambda}\cos(\omega_s t)\right) \tag{6b}$$

7. In the case where the acoustic intensity $I_s$ is less than several watts/cm², which is always true, $\Delta \ll \lambda$, and formula 6(b) becomes $$I \approx I_{Lr} + I_{Lp} + 2\sqrt{I_{Lr}I_{Lp}} \cdot 2\Delta \cdot \frac{2\pi}{\lambda}\cos(\omega_s t) \tag{7}$$

8. When the photodiode is followed by a high pass filter which blocks d.c. and low frequency components, as it normally is, the resultant output signal applied as an input to a peak detector becomes proportional to $$I_{Lh} \approx \frac{8\pi}{\lambda}\sqrt{I_{Lr}I_{Lp}}\,\Delta\cos(\omega_s t) \tag{8}$$

where $I_{Lh}$ is the high frequency component (third term) of formula (7).

9. In the case of optical path wiggling, under the conditions that $2\phi_w > \lambda/2$ and $\Delta \ll \lambda$, formula (5b) reduces to $$I_L \approx 2A_rA_p[\cos(\phi_0+\phi_w\cos(W_\omega t))$$
$$-\sin(\phi_0+\phi_w\cos(W_\omega t))\sin(2\Delta \cdot \frac{2\pi}{\lambda}\cos(\omega_s t))] \tag{9}$$

where $\phi_w$ is half the peak-to-peak phase excursion of interfering reference wave due to optical path wiggling, $\phi_0 = (\phi_p - \phi_r)$, $W_\omega = 2\pi f_w$, $f_w$ is the wiggling frequency.

10. The second term of formula (9), consisting of the ultrasonic wave frequency amplitude modulated by the wiggling frequency, is the high frequency component which is peak detected. The excursion of phase angle $\phi_0 + \phi_w \cos(W_\omega t)$ is $$\begin{matrix} 0 & & \pi \\ & >(\phi_0+\phi_w\cos(W_\omega t)) & \\ -\pi & & 0 \end{matrix} \tag{10a}$$

When instantaneous value of $(\phi_0+\phi_w\cos(W_\omega t)) = 0$ or $\pm\pi$, $$2A_rA_p\sin(\phi_0+\phi_\omega\cos(W_\omega t))\sin(2\Delta \cdot \frac{2\pi}{\lambda}\cos(W_s t)) = 0 \tag{10b}$$

When instantaneous value of $\phi_0\phi_w\cos(W_\omega t) = \pm\pi/2$, $$\frac{2\pi}{\lambda}\cos(W_s t)) = \pm\frac{8\pi}{\lambda}A_r+A_p\Delta\cos(W_s t) \tag{10c}$$

11. The first term of formula (9), consisting of a function of the wiggler frequency alone, can be rewritten as $$I_w = 2A_rA_p\cos(\phi_0+\phi_w\cos(W_\omega t)) \tag{11a}$$

Transforming formula (11a) to Bessel function form results in $$I_w = 2A_rA_p \sum_n (\alpha)^{2n} J_{2n}(\phi_w)\cos(2_n W_\omega t) \tag{11b}$$

where $n$ is the ordinal member of each multiple (harmonic) of the fundamental frequency, $f_w$, $2n$ is each even multiple thereof, $(\alpha)^{2n}$ is the relative amplitude of each even harmonic, and $\phi_0=0$ (when $\phi_0 \neq 0$, the result is similar but more tedious).

A wiggler harmonic $n_w$, where $$n_w \approx \frac{\omega_s}{2W_\omega},$$

can cause unwanted interference with the ultrasonic wave, if its amplitude is sufficient.

However, a property of Bessel function is that $J_n(\phi) \approx 0$ for $n > \phi$.

Therefore, interference is avoided when $$\frac{\omega_s}{2W_\omega} = n_w > \phi_w \tag{11c}$$

$$W_\omega < \frac{\omega_s}{2\phi_w} \tag{11d}$$

However, principles of invention require $\phi_w > \pi/2$ by at least a certain amount determined by the rate of random drift and $W_\omega$ to be sufficiently high to permit at least one sample of an insonified spot on the pellicle by a scanning light beam during each wiggling half-cycle. Therefore, within these constraints, in order to avoid unwanted interference, optical path wiggling frequency (i.e. $W_\omega$) and wiggling amplitude (i.e. $\phi_\omega$) should be selected to conform to formula (11d).

What is claimed is:

1. In a system responsive to the intensity of radiated ultrasonic wave energy having a first given frequency; the combination comprising:

a. first means including a detection means responsive to the illumination thereof with interfering first and second components of coherent light of predetermined wavelength $\lambda$ for deriving an output signal substantially proportional to the peak phase change at said first given frequency in said first and second light components;

b. second means including an interferometer for illuminating said detection means with said first and second interfering light components, wherein said interferometer comprises a substantially rigid reference mirror illuminated by said first light component and a flexible pellicle mirror of given surface area having a selected spot thereof illuminated by said second light component; said selected spot on said flexible pellicle mirror, in response to being insonified by said ultrasonic wave energy, vibrating at said first given frequency through an acoustic displacement amplitude $\Delta$ determined by the intensity of said ultrasonic wave energy insonifying said selected spot, wherein $\Delta << \lambda$, and c. third means for wiggling at a second given frequency the round-trip optical path length of said first light component reflected from said rigid reference mirror by an amount which is greater than $\lambda/2$, said second given frequency being significantly lower than said first given frequency, d. whereby said output signal derived by said detection means is substantially proportional to the acoustic displacement amplitude $\Delta$ of said selected spot.

2. The combination defined in claim 1, wherein said third means includes an electro-optic modulator in said optical path of solely said first light component for varying said first light component optical path length at said second given frequency.

3. The combination defined in claim 1, wherein said second means includes a laser for generating a beam of coherent light of wavelength $\lambda$, and wherein said interferometer further comprises a beam splitter for separating said beam of coherent light into said first and second light components prior to the reflection of said first light component from said rigid reference mirror and said second light component from said flexible pellicle mirror, said beam splitter recombining said first and second light components subsequent to the aforesaid reflection thereof and directing said recombined first and second light components toward said detection means.

4. The combination defined in claim 1, further including means for insonifying said flexible pellicle mirror.

5. The combination defined in claim 1, wherein said third means includes a mechanical vibrator attached to said rigid reference mirror for vibrating said reference mirror at said second given frequency.

6. The combination defined in claim 5, wherein said mechanical vibrator is a piezoelectric vibrator.

7. The combination defined in claim 1, wherein said flexible pellicle mirror comprises an annular frame, a reflecting pellicle attached to one side of said frame and completely covering the opening defined by said frame on said one side thereof, a backing plate attached to the other side of said frame and completely covering the opening defined by said frame on said other side thereof, the enclosed volume between said pellicle and said backing plate being filled with a liquid.

8. The combination defined in claim 7, wherein said liquid is water.

9. The combination defined in claim 1, wherein said detection means includes a photodiode light detector illuminated by said interfering first and second light components, a peak detector, and a high pass filter coupling the output of said photodiode light detector to the input of said peak detector, said high pass filter passing said first given frequency and substantially filtering out the d.c. component, said second given frequency and all frequencies below said second given frequency in the output of said photodiode light detector.

10. The combination defined in claim 9, wherein said peak detector is a normally disabled gated peak detector, and wherein said combination further includes pulse-operated means for insonifying said flexible pellicle mirror at a predetermined repetition rate with short duty-cycle pulses of ultrasonic wave energy, and coupling means between said pulse-operated means and said gated peak detector for applying gating signal pulses to said gated peak detector to effect the enabling thereof approximately only during the interval while said flexible pellicle mirror is being insonified by a pulse of ultrasonic wave energy.

11. The combination defined in claim 1, wherein said second means includes second light component deflection means for selecting said illuminated spot on said flexible pellicle mirror in accordance with at least one deflection control signal applied thereto, and wherein said first means includes a deflection control signal generator for applying said deflection control signal to said deflecting means.

12. The combination defined in claim 11, wherein said deflection means is situated between said beam splitter and said insonified flexible pellicle mirror in the path of only said second light component.

13. The combination defined in claim 11, wherein said first means includes indicating means having said output signal derived by said detection means coupled as an input thereto for indicating the magnitude thereof.

14. The combination defined in claim 13, wherein said first means includes a cathode-ray tube display coupled to said deflection control generator for deflecting the electron beam of said display in correspondence with the deflection of said selected spot, and coupling means for applying said output signal derived by said detection means to said display for intensity modulating the electron beam of said display in accordance therewith.

15. The combination defined in claim 14, wherein said deflection control signal applies given deflection control signals to said deflecting means and said display to repetitively raster scan said selected spot over the surface area of said flexible pellicle mirror and repetitively raster scan said electron beam of said display in synchronism with each other.

\* \* \* \* \*